United States Patent
Martinelli

(10) Patent No.: US 6,747,539 B1
(45) Date of Patent: Jun. 8, 2004

(54) PATIENT-SHIELDING AND COIL SYSTEM

(76) Inventor: Michael A. Martinelli, 58 Wedgemere Ave., Winchester, MA (US) 01890

(*) Notice: Subject to any disclaimer, the term of this patent is extended or adjusted under 35 U.S.C. 154(b) by 538 days.

(21) Appl. No.: 09/698,895

(22) Filed: Oct. 27, 2000

Related U.S. Application Data

(60) Provisional application No. 60/161,989, filed on Oct. 28, 1999.

(51) Int. Cl.$^7$ ............................................... H01F 27/02
(52) U.S. Cl. .................................. 336/84 C; 128/899
(58) Field of Search ............................... 336/200, 232, 336/84 R, 84 C, 84 M; 600/9, 6, 15, 422, 119; 128/897, 899

(56) References Cited

U.S. PATENT DOCUMENTS

| | | | |
|---|---|---|---|
| 3,674,017 A | 7/1972 | Tillander | 128/2.05 |
| 3,868,565 A | 2/1975 | Kuipers | 324/41 |
| 4,054,881 A | 10/1977 | Raab | 343/112 |
| 4,173,228 A | 11/1979 | Van Steenwyk et al. | 128/653 |
| 4,262,306 A | 4/1981 | Renner | 358/93 |
| 4,287,809 A | 9/1981 | Egli et al. | 89/41 |
| 4,314,251 A | 2/1982 | Raab | 343/112 |
| 4,317,078 A | 2/1982 | Weed et al. | 324/208 |
| 4,339,953 A | 7/1982 | Iwasaki | 73/654 |
| 4,396,885 A | 8/1983 | Constant | 324/208 |
| 4,422,041 A | 12/1983 | Lienau | 324/207 |
| 4,431,005 A | 2/1984 | McCormick | 128/656 |
| 4,548,208 A | 10/1985 | Niemi | 128/419 |
| 4,572,198 A | 2/1986 | Codrington | 128/653 |
| 4,613,866 A | 9/1986 | Blood | 343/448 |
| 4,618,978 A | 10/1986 | Cosman | 378/164 |
| 4,642,786 A | 2/1987 | Hansen | 364/559 |
| 4,649,504 A | 3/1987 | Krouglicof et al. | 364/559 |
| 4,737,794 A | 4/1988 | Jones | 342/448 |
| 4,821,731 A | 4/1989 | Martinelli et al. | 128/662.06 |
| 4,836,778 A | 6/1989 | Baumrind et al. | 433/69 |
| 4,849,692 A | 7/1989 | Blood | 324/208 |
| 4,889,526 A | 12/1989 | Rauscher et al. | 600/14 |
| 4,905,698 A | 3/1990 | Strohl, Jr. et al. | 128/653 |

(List continued on next page.)

FOREIGN PATENT DOCUMENTS

| | | |
|---|---|---|
| EP | 0419729 A1 | 9/1989 |
| EP | 0655138 B1 | 8/1993 |
| EP | 0894473 A2 | 1/1995 |
| WO | WO 91/07726 | 5/1991 |
| WO | WO 92/06645 | 4/1992 |
| WO | WO 94/04938 | 3/1994 |

OTHER PUBLICATIONS

Edward C. Benzel et al., "Magnetic Source Imaging: a Review of the Magnes System of Biomagnetic Technologies Incorporated," Nurosurgery, vol. 33, No. 2 (Aug. 1993), p. 252–259.

*Primary Examiner*—Tuyen T. Nguyen
(74) *Attorney, Agent, or Firm*—Harness, Dickey & Pierce, P.L.C.

(57) ABSTRACT

A patient-shielding and coil system, including a coil wire electrically coupled to a source of electrical current, an electrically conductive surface, insulation material situated between the coil wire and the conductive surface, and a drain wire connected to the conductive surface and forming a capacitive current loop with respect to the source.

17 Claims, 8 Drawing Sheets

U.S. PATENT DOCUMENTS

| | | | | |
|---|---|---|---|---|
| 4,945,305 | A | 7/1990 | Blood | 324/207 |
| 4,977,655 | A | 12/1990 | Martinelli | 29/25.35 |
| 4,989,608 | A | 2/1991 | Ratner | 128/653 |
| 4,991,579 | A | 2/1991 | Allen | 128/653 |
| 5,002,058 | A | 3/1991 | Martinelli | 128/662 |
| 5,005,592 | A | 4/1991 | Cartmell | 128/899 |
| 5,016,639 | A | 5/1991 | Allen | 128/653 |
| 5,030,196 | A | 7/1991 | Inoue | 600/14 |
| 5,042,486 | A | 8/1991 | Pfeiler et al. | 128/653 |
| 5,050,608 | A | 9/1991 | Watanabe et al. | 128/653 |
| 5,054,492 | A | 10/1991 | Scribner et al. | 128/662.06 |
| 5,059,789 | A | 10/1991 | Salcudean | 250/206.1 |
| 5,086,401 | A | 2/1992 | Glassman et al. | 395/94 |
| 5,099,845 | A | 3/1992 | Besz et al. | 128/653.1 |
| 5,105,829 | A | 4/1992 | Fabian et al. | 128/899 |
| 5,152,288 | A | 10/1992 | Hoenig et al. | 128/653.1 |
| 5,161,536 | A | 11/1992 | Vilkomerson et al. | 128/660.07 |
| 5,187,475 | A | 2/1993 | Wagener et al. | 340/870.32 |
| 5,197,476 | A | 3/1993 | Nowacki et al. | 128/660.03 |
| 5,198,768 | A | 3/1993 | Keren | 324/318 |
| 5,198,877 | A | 3/1993 | Schulz | 356/375 |
| 5,211,164 | A | 5/1993 | Allen | 128/653.1 |
| 5,211,165 | A | 5/1993 | Dumoulin et al. | 128/653.1 |
| 5,214,615 | A | 5/1993 | Bauer | 367/128 |
| 5,222,499 | A | 6/1993 | Allen et al. | 128/653.1 |
| 5,228,442 | A | 7/1993 | Imran | 128/642 |
| 5,249,581 | A | 10/1993 | Horbal et al. | 128/664 |
| 5,251,635 | A | 10/1993 | Dumoulin et al. | 128/653.2 |
| 5,253,647 | A | 10/1993 | Takahashi et al. | 128/653.1 |
| 5,255,680 | A | 10/1993 | Darrow et al. | 128/653.1 |
| 5,257,636 | A | 11/1993 | White | 128/897 |
| 5,265,610 | A | 11/1993 | Darrow et al. | 128/653.1 |
| 5,265,611 | A | 11/1993 | Hoenig et al. | 128/653.1 |
| 5,269,759 | A | 12/1993 | Hernandez et al. | 604/96 |
| 5,271,400 | A | 12/1993 | Dumoulin et al. | 128/653.2 |
| 5,273,025 | A | 12/1993 | Sakiyama et al. | 128/6 |
| 5,274,551 | A | 12/1993 | Corby, Jr. | 364/413.13 |
| 5,279,309 | A | 1/1994 | Taylor et al. | 128/782 |
| 5,295,483 | A | 3/1994 | Nowacki et al. | 128/660.03 |
| 5,299,254 | A | 3/1994 | Dancer et al. | 378/163 |
| 5,299,288 | A | 3/1994 | Glassman et al. | 395/80 |
| 5,309,913 | A | 5/1994 | Kormos et al. | 128/653.1 |
| 5,315,630 | A | 5/1994 | Sturm et al. | 378/64 |
| 5,316,024 | A | 5/1994 | Hirschi et al. | 128/899 |
| 5,318,025 | A | 6/1994 | Dumoulin et al. | 128/653.2 |
| 5,325,728 | A | * 7/1994 | Zimmerman et al. | 73/861.12 |
| 5,325,873 | A | 7/1994 | Hirschi et al. | 128/899 |
| 5,353,795 | A | 10/1994 | Souza et al. | 128/653.2 |
| 5,368,030 | A | 11/1994 | Zinreich et al. | 128/653.1 |
| 5,375,596 | A | 12/1994 | Twiss et al. | 128/653.1 |
| 5,377,678 | A | 1/1995 | Dumoulin et al. | 128/653.1 |
| 5,383,454 | A | 1/1995 | Bucholz | 128/653.1 |
| 5,386,828 | A | 2/1995 | Owens et al. | 128/653.1 |
| 5,389,101 | A | 2/1995 | Heilbrun et al. | 606/130 |
| 5,391,199 | A | 2/1995 | Ben-Haim | 607/122 |
| 5,402,801 | A | 4/1995 | Taylor | 128/898 |
| 5,408,409 | A | 4/1995 | Glassman et al. | 364/413.13 |
| 5,417,210 | A | 5/1995 | Funda et al. | 128/653.1 |
| 5,419,325 | A | 5/1995 | Dumoulin et al. | 128/653.2 |
| 5,425,367 | A | 6/1995 | Shapiro et al. | 128/653.1 |
| 5,425,382 | A | 6/1995 | Golden et al. | 128/899 |
| 5,429,132 | A | 7/1995 | Guy et al. | 128/653.1 |
| 5,437,277 | A | 8/1995 | Dumoulin et al. | 128/653.1 |
| 5,443,066 | A | 8/1995 | Dumoulin et al. | 128/653.1 |
| 5,443,489 | A | 8/1995 | Ben-Haim | 607/115 |
| 5,445,144 | A | 8/1995 | Wodicka et al. | 128/207.14 |
| 5,445,150 | A | 8/1995 | Dumoulin et al. | 128/653.1 |
| 5,445,166 | A | 8/1995 | Taylor | 128/897 |
| 5,453,686 | A | 9/1995 | Anderson | 324/207.17 |
| 5,456,718 | A | 10/1995 | Szymaitis | 623/11 |
| 5,480,422 | A | 1/1996 | Ben-Haim | 607/122 |
| 5,483,961 | A | 1/1996 | Kelly et al. | 128/653.1 |
| 5,487,729 | A | 1/1996 | Avellanet et al. | 604/96 |
| 5,513,637 | A | 5/1996 | Twiss et al. | 128/653.1 |
| 5,517,990 | A | 5/1996 | Kalfas et al. | 128/653.1 |
| 5,542,938 | A | 8/1996 | Avellanet et al. | 604/280 |
| 5,546,951 | A | 8/1996 | Ben-Haim | 128/702 |
| 5,558,091 | A | 9/1996 | Acker et al. | 128/653.1 |
| 5,568,809 | A | 10/1996 | Ben-haim | 128/656 |
| 5,572,999 | A | 11/1996 | Taylor et al. | 128/653.1 |
| 5,588,430 | A | 12/1996 | Bova et al. | 128/653.1 |
| 5,592,939 | A | 1/1997 | Martinelli | 128/653.1 |
| 5,600,330 | A | 2/1997 | Blood | 342/463 |
| 5,603,318 | A | 2/1997 | Heilbrun et al. | 128/630 |
| 5,617,857 | A | 4/1997 | Chader et al. | 128/653.1 |
| 5,622,169 | A | 4/1997 | Golden et al. | 128/653.1 |
| 5,622,170 | A | 4/1997 | Schulz | 128/653.1 |
| 5,630,431 | A | 5/1997 | Taylor | 128/897 |
| 5,640,170 | A | 6/1997 | Anderson | 343/895 |
| 5,645,065 | A | 7/1997 | Shapiro et al. | 128/653.1 |
| 5,647,361 | A | 7/1997 | Damadian | 128/683.2 |
| 5,662,111 | A | 9/1997 | Cosman | 128/653.1 |
| 5,676,673 | A | 10/1997 | Ferre et al. | 606/130 |
| 5,694,945 | A | 12/1997 | Ben-Haim | 128/736 |
| 5,695,500 | A | 12/1997 | Taylor et al. | 606/130 |
| 5,711,299 | A | 1/1998 | Manwaring et al. | 128/653.1 |
| 5,713,946 | A | 2/1998 | Ben-Haim | 607/122 |
| 5,718,241 | A | 2/1998 | Ben-Haim et al. | 128/702 |
| 5,729,129 | A | 3/1998 | Acker | 324/207.12 |
| 5,730,129 | A | 3/1998 | Darrow et al. | 128/653.1 |
| 5,732,703 | A | 3/1998 | Kalfas et al. | 128/653.1 |
| 5,735,278 | A | * 4/1998 | Hoult et al. | 600/422 |
| 5,738,096 | A | 4/1998 | Ben-Haim | 128/653.1 |
| 5,749,362 | A | 5/1998 | Funda et al. | 128/653.1 |
| 5,752,513 | A | 5/1998 | Acker et al. | 128/653.1 |
| 5,758,667 | A | 6/1998 | Slettenmark | 128/899 |
| 5,762,064 | A | 6/1998 | Polvani | 128/653.1 |
| 5,776,064 | A | 7/1998 | Kalfas et al. | 600/414 |
| 5,787,886 | A | 8/1998 | Kelly et al. | 128/653.1 |
| 5,800,352 | A | 9/1998 | Ferre et al. | 600/407 |
| 5,803,089 | A | 9/1998 | Ferre et al. | 128/897 |
| 5,810,728 | A | 9/1998 | Kuhn | 600/410 |
| 5,829,444 | A | 11/1998 | Ferre et al. | 128/897 |
| 5,831,260 | A | 11/1998 | Hansen | 250/221 |
| 5,833,608 | A | 11/1998 | Acker | 600/409 |
| 5,836,954 | A | 11/1998 | Heilbrun et al. | 600/130 |
| 5,840,024 | A | 11/1998 | Taniguchi et al. | 600/424 |
| 5,840,025 | A | 11/1998 | Ben-Haim | 600/424 |
| 5,851,183 | A | 12/1998 | Bucholz | 600/425 |
| 5,868,674 | A | 2/1999 | Glowinski et al. | 600/410 |
| 5,871,445 | A | 2/1999 | Bucholz | 600/407 |
| 5,873,822 | A | 2/1999 | Ferre et al. | 600/407 |
| 5,891,034 | A | 4/1999 | Bucholz | 600/426 |
| 5,913,820 | A | 6/1999 | Bladen et al. | 600/407 |
| 5,920,395 | A | 7/1999 | Schulz | 356/375 |
| 5,950,629 | A | 9/1999 | Taylor et al. | 128/897 |
| 5,954,647 | A | 9/1999 | Bova et al. | 600/407 |
| 5,967,980 | A | 10/1999 | Ferre et al. | 600/424 |
| 5,976,156 | A | 11/1999 | Taylor et al. | 606/130 |
| 5,987,349 | A | 11/1999 | Schulz | 600/427 |
| 6,019,725 | A | 2/2000 | Vesely et al. | 600/447 |
| 6,024,695 | A | 2/2000 | Taylor et al. | 600/102 |
| 6,104,944 | A | 8/2000 | Martinelli | 600/424 |
| 6,122,538 | A | 9/2000 | Sliwa, Jr. et al. | 600/407 |
| 6,131,396 | A | * 10/2000 | Duerr et al. | 62/51.1 |
| 6,161,032 | A | 12/2000 | Acker | 600/424 |

* cited by examiner

PATIENT-SHIELDING AND COIL SYSTEM

CROSS-REFERENCE TO RELATED APPLICATIONS

The following United States patent applications, which were concurrently filed with this one on Oct. 28, 1999, are fully incorporated herein by reference: Method and System for Navigating a Catheter Probe in the Presence of Field-influencing Objects, by Michael Martinelli, Paul Kessman and Brad Jascob, Ser. No. 60/161,991; Coil Structures and Methods for Generating Magnetic Fields, by Brad Jascob, Paul Kessman and Michael Martinelli, Ser. No. 60/161,990; Navigation Information Overlay onto Ultrasound Imagery, by Paul Kessman, Troy Holsing and Jason Trobaugh Ser. No. 09/428,720; Registration of Human Anatomy Integrated for Electromagnetic Localization, by Mark W. Hunter and Paul Kessman, Ser. No. 09/429,569; System for Translation of Electromagnetic and Optical Localization Systems, by Mark W. Hunter and Paul Kessman, Ser. No. 09/429,568; Surgical Communication and Power System, by Mark W. Hunter, Paul Kessman and Brad Jascob, Ser. No. 09/428,722; and Surgical Sensor, by Mark W. Hunter, Sheri McCoid and Paul Kessman, Ser. No. 09/428,721.

This application claims the benefit of U.S. Provisional Application No. 60/161,989, filed Oct. 28, 1999, now abandoned the contents of which are incorporated herein by reference in their entirety, and from which priority is claimed.

STATEMENT REGARDING FEDERALLY SPONSORED RESEARCH

Not Applicable

REFERENCE TO MICROFICHE APPENDIX

Not Applicable

BACKGROUND OF THE INVENTION

The present invention relates to, a patient-shielding system for use when a patient is exposed to capacitive currents as a result of immersion into a time-varying magnetic field. More particularly, this invention relates to a system for redirecting potentially harmful currents away from organs such as the heart when a medical procedure includes exposing that organ to a time-varying magnetic field.

Systems and methods for determining the position and orientation of surgical probes based on the use of magnetic fields are known. See, for example, U.S. Pat. No. 5,592,939. Such systems and methods generally rely on the presence of a time varying magnetic field in the surgical region of interest. An exemplary navigation system is shown in FIG. 1. The exemplary system of FIG. 1 contains platform 10 in which is embedded coils for generating a time-varying magnetic field. Two such coils are depicted as first coil set 12 and second coil set 14. Field line 22 depicts the orientation of a magnetic field amplitude at an instant of time. See also U.S. Pat. No. 5,592,939.

Present techniques for projecting a time varying magnetic field into a surgical region of interest preferably position the patient proximal to the coils that are generating the necessary fields. This is depicted in FIG. 2. Patient 24 is generally kept from direct contact with coil sets 12 and 14 by non-conducting layer 20. As a result of this relationship, there are times when coil sets 12 and 14, located proximally to the surgical region of interest, may have differing voltage potentials. By way of example only, in FIG. 2, coil set 12 is at positive potential 16, and coil set 14 is at negative potential 18. A uniform amplitude field that has its major component lateral to a plane determined by an operating room table is thus generated by two coils at different voltage potentials separated along that lateral dimension. Field line 22 in FIG. 2 indicates the direction of such an amplitude. In the relationship indicated in FIG. 2, the surgical region of interest has loop characteristics of what is known as a capacitive current. A schematic of such a current is depicted in FIG. 3. For a time-varying magnetic field where the frequency is of the order of f=20 kilohertz and the difference between positive potential 16 and negative potential 18 is V=25 volts, capacitive current 34, denoted by I, can exceed what is considered desirable. For example, typical safety standards, such as those of Underwriter Laboratories, require that the current through a patient be less than I=10 microamps. For insulating layer 20 with capacitance 30 of the order of $C=10^{-10}$ farads, and where patient 24 has a resistance 32 of approximately 100 ohms, capacitive current 34 is of the order $$I = V(2\pi fC) = 345 \text{ microamps}$$

This is well in excess of a 10 microamp current.

In light of the foregoing, it is desirable to reduce the magnitude of the capacitive current introduced by a magnetic field coil within a surgical region. It is an object of the present invention to substantially overcome the above-identified disadvantages and drawbacks of the prior art.

SUMMARY OF THE INVENTION

The foregoing and other objects are achieved by the invention which in one aspect comprises a patient-shielding and coil system, including a coil wire electrically coupled to a source of electrical current, an electrically conductive surface, insulation material situated between the coil wire and the conductive surface, and a drain wire connected to the conductive surface and forming a capacitive current loop with respect to the source.

In another embodiment of the invention, the conductive surface has a resistance of substantially 1 ohm per square.

In another embodiment of the invention, the electrically conductive surface forms an incomplete enclosure of the coil wire, so as to create an incomplete electrical circuit.

In another embodiment of the invention, the conductive surface includes an upper portion and a lower portion.

In another embodiment of the invention, the conductive surface includes a polyester foil, vapor deposited with aluminum.

BRIEF DESCRIPTION OF DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENTS

The present invention is directed to a system for redirecting potentially harmful currents away from organs such as the heart when a medical procedure includes exposing that organ to a time-varying magnetic field.

Figure 1:
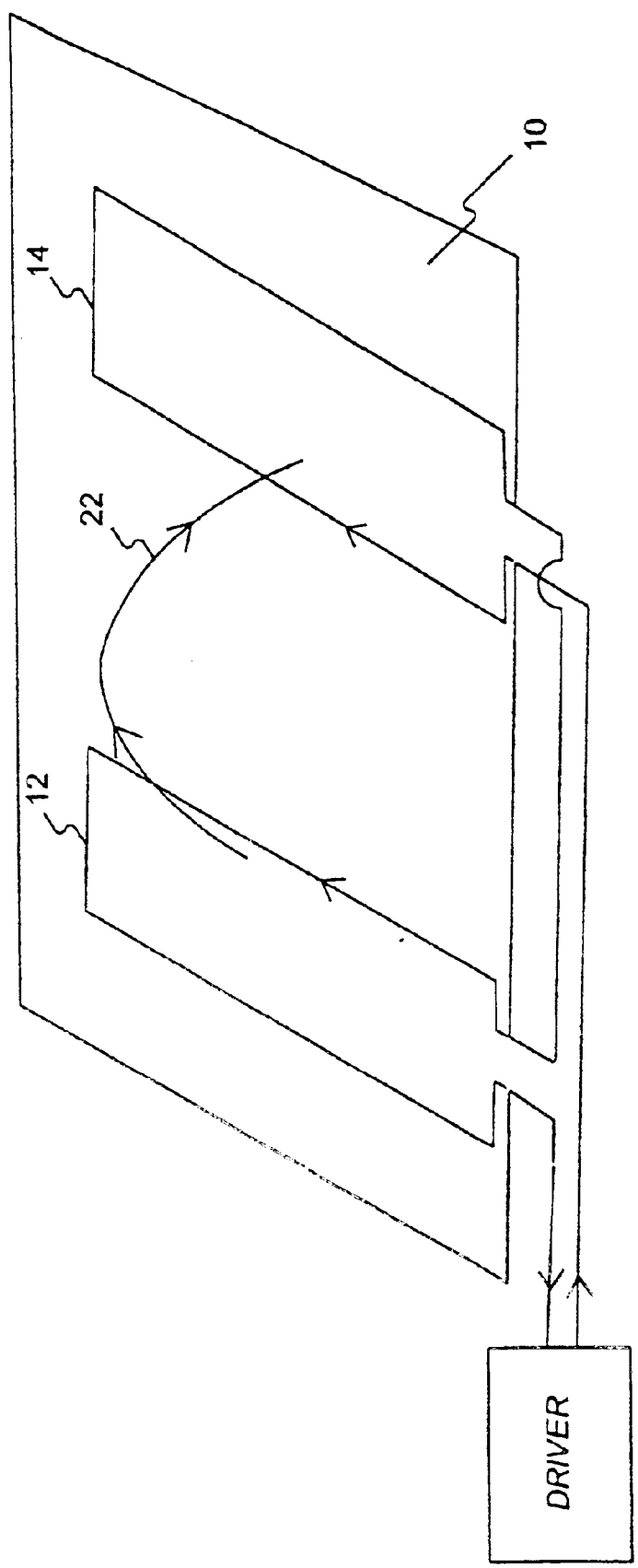
FIG. 1 depicts an exemplary coil system for generating a uniform amplitude magnetic field for a navigational system.
Figure 2:
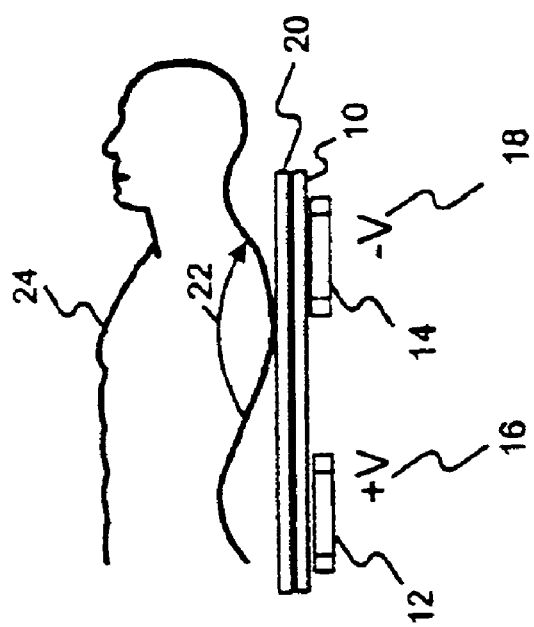
FIG. 2 depicts an effect the exemplary system of FIG. 1 can have on a patient.
Figure 3:
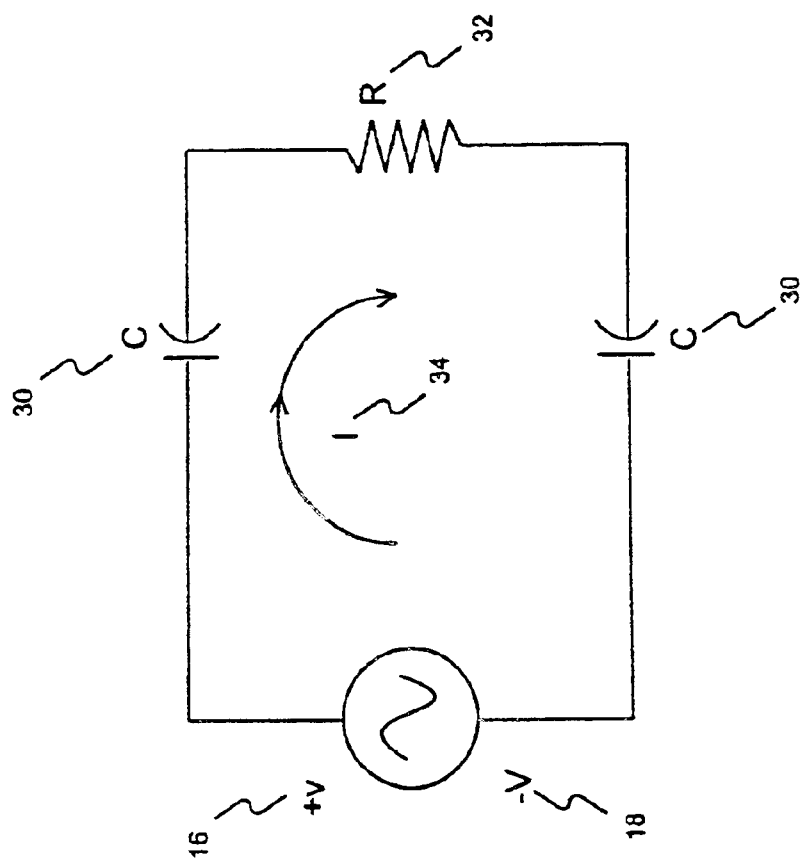
FIG. 3 is a circuit diagram of a capacitive current loop formed by the configuration of FIG. 2.
Figure 4:
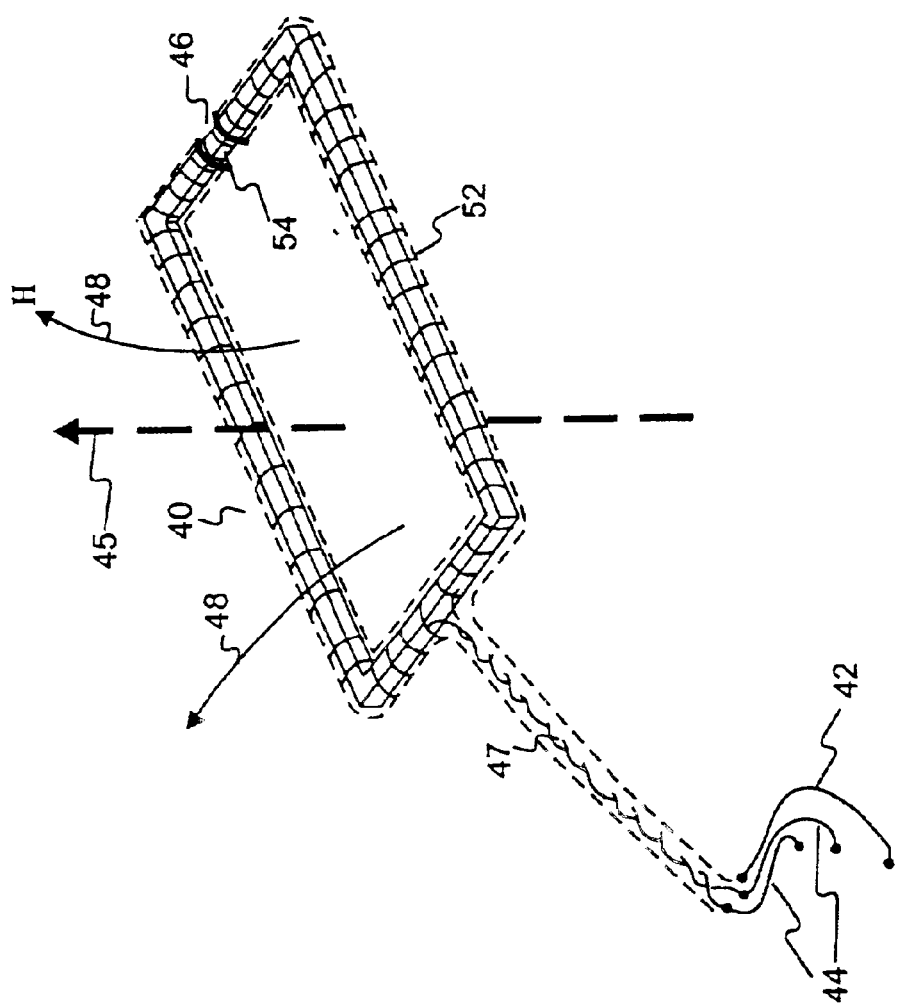
FIG. 4 depicts an exemplary patient-shielding and coil system consistent with the present invention.

FIG. 4 depicts a patient-shielding and coil system in accordance with a preferred embodiment of the present invention. The ends of coil wire 44 are attached to a driving voltage source (not shown). Between the ends of coil wire 44 and the coil assembly 40, coil wire 44 is wrapped about itself as twisted pair 47. Within coil assembly 40, coil wire 44 is looped N times. The current along coil wire 40 is denoted $I_M$. Thus, in the absence of any other effects, the net current around coil assembly 40 is $NI_M$.

Also depicted in FIG. 4 is coil form 54. Coil form 54 surrounds that portion of coil wire 44 where coil wire 44 is looped N times. Coil form 54 is depicted in FIG. 4 as rectangular in shape, but other shapes such can be used as well, and are consistent with the present invention. Other embodiments of the invention may include a coil wire 44 without a coil form, such that the coil wire is looped without the benefit of any coil form.

Also depicted in FIG. 4 is drain wire 42 and shield 52, depicted as the dashed line. The shield 52 is preferably electrically conductive, so as to support an electrical current in the presence of a voltage potential. In some embodiments, the shield 52 may include a nonconductive foundation bonded, or otherwise attached, to a conductive surface. Drain wire 42 is attached, or otherwise mounted, to shield 52. Shield 52 extends along twisted pair 47 and envelops most of coil form 54, and thus envelopes most of coil wire 44. However, shield 52 does not form a complete enclosure around coil axis 45, so as to prevent a compensating current from forming along the surface of shield 52 that would serve to decrease the magnitude of the magnetic field produced by the coil assembly 40. Thus, shield 52 ends at gap 46.

Figure 5:
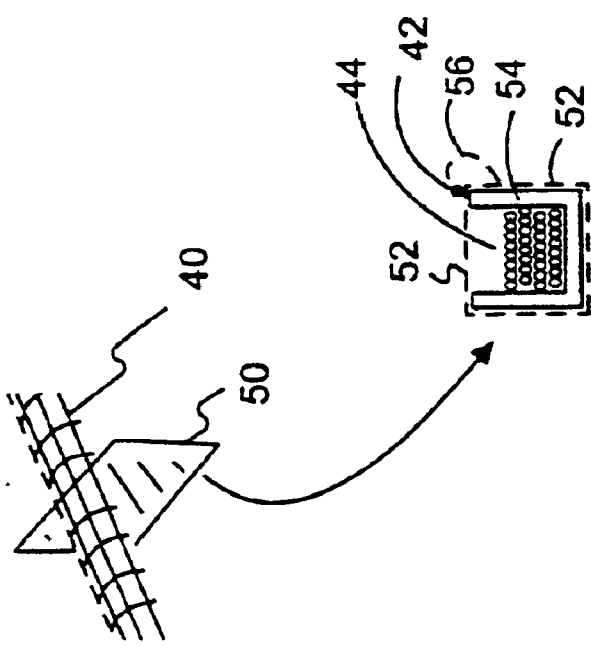
FIG. 5 depicts a cross section of a portion of the exemplary system of FIG. 4.

A more detailed cross section of coil assembly 40 consistent with a preferred embodiment of the present invention is shown in FIG. 5. Shield 52 is exterior of coil form 54. The lower portion of shield 52 is depicted as "U" shaped, and the upper portion of shield 52 is depicted as a cover. The lower and upper portions of shield 52 can preferably be connected by conductive silver ink at location 56, but other techniques of connectivity using any type of conducting material can also be used. Shield 52 can be composed of a polyester foil with aluminum vapor-deposited on its surface, but other compositions with the resistance discussed below can also be used. The resistance of the vapor-deposited aluminum, a thin film, used in one embodiment of the present invention is of the order 1 ohm per square. The unit "ohm per square" is a unit of resistance known in the art appropriate for discussions of thin film material. Drain wire 42 is connected to shield 52 and is connected to ground. Drain wire 42 carries the current $I_C$ along the length of shield 52. At each point along shield 52 the current $I_C$ in drain wire 42 is the total of all current induced between that point and gap 46. Because of the ground connection, these are capacitive currents as discussed above with regard to patient 24. However, here the capacitive current loop is closed with respect to a ground rather than through patient 24. The current $I_C$, at an instant of time, is associated with positive potential 16 and the capacitance of coil form 54, where the current loop of interest is completed by shield 52 connected to ground via drain wire 42.

Figure 6:
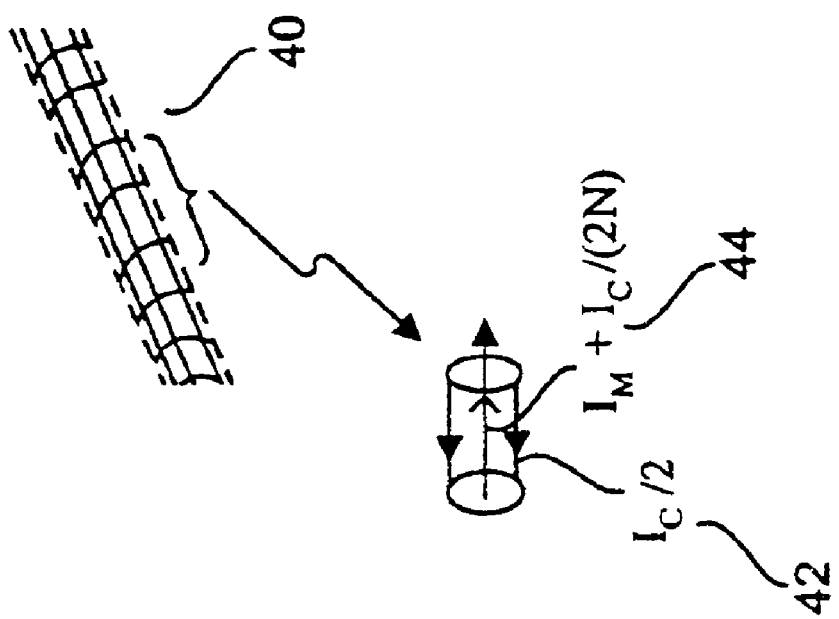
FIG. 6 depicts an example of how current flows across a cross section of the exemplary system of FIG. 4.

Also depicted in the cross section shown in FIG. 5 are the N cross sections of coil wire 44 contained within coil form 54. Because of the presence of current $I_C$ along drain wire 42, the current in coil wire 44 is altered by an amount of the order $I_C/(2N)$. This is depicted in FIG. 6 where drain wire 42 along shield 52 has a current $-I_C/2$ and coil wire 44 along one loop has an adjusted current $I_M+I_C/(2N)$. The net current including the effect of N loops of coil wire 44 and drain wire 42 along coil assembly 40, however, remains the value as before $NI_M$. The current along drain wire 42 is cancelled. The net result is that patient 24 is shielded from capacitive current 34 by an amount of the order $I_C$. Nevertheless, the desired magnetic fields for navigation throughout the surgical region of interest remain the same.

Figure 7:
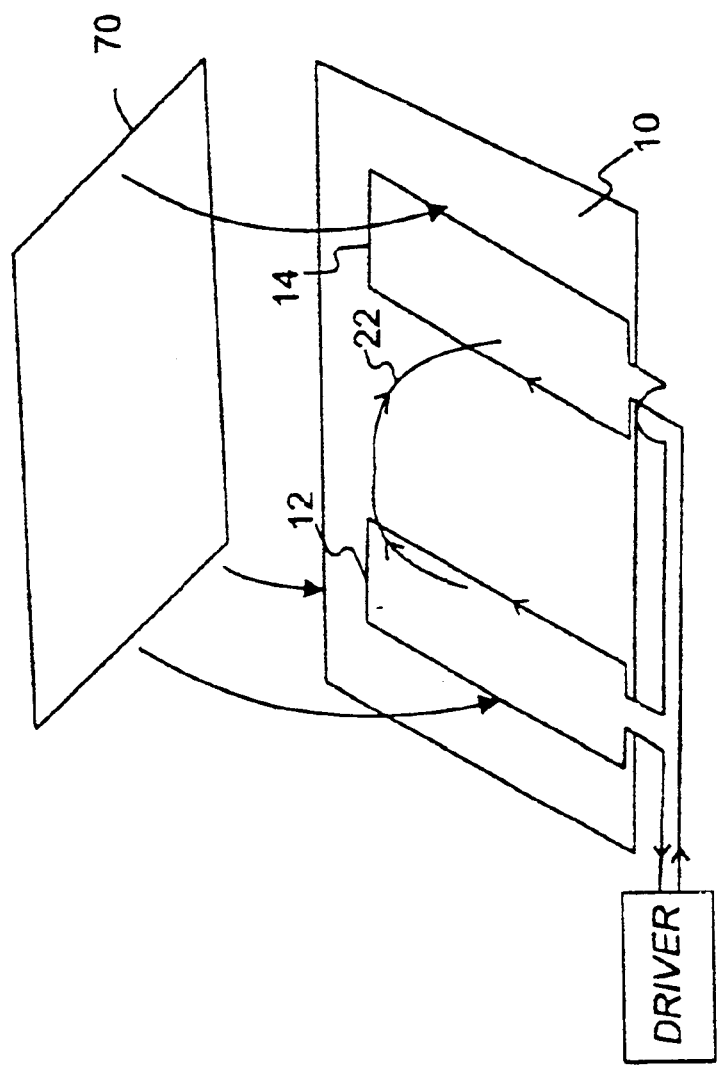
FIG. 7 depicts an alternative exemplary patient-shielding and coil system consistent with the present invention.
Figure 8:
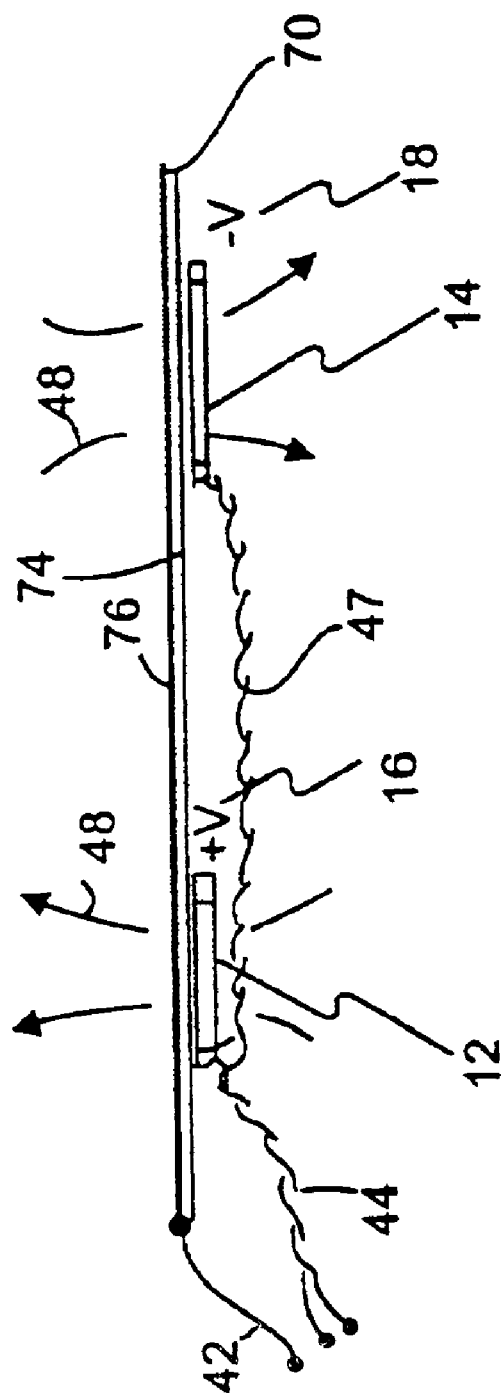
FIG. 8 depicts a side view of the exemplary patient-shielding and coil system of FIG. 7.

FIGS. 7 and 8 depict a patient-shielding and coil system in accordance with another preferred embodiment of the present invention. In FIGS. 7 and 8, shield system 70 is placed over platform 10 containing coil sets 12 and 14. Shield system 70 is depicted as containing vapor-deposited conductive film 76 on top of non-conductive plastic sheet 74. Conductive film 76 is connected to drain wire 42. Coil sets 12 and 14 are connected in series and are driven through twisted pair 47 to produced the desired magnetic fields. Positive potential 16 and negative potential 18 are shielded from patient 24 the conductive film 76. Vapor-deposited conductive film 76 has a resistance of the order 1 ohm per square. This resistance is sufficient to produce little effect on the magnetic fields, indicated in FIG. 8 by field lines 48. Nevertheless, this resistance is sufficient to protect patient 24 from capacitive current 34.

Experiments performed to measure the effect on navigation of the currents induced in the shield system 70 indicate that these currents are small and have an effect of less than 0.1% on navigation accuracy. The small residual effect can be eliminated by a calibration of the navigating fields in the presence of shield system 70.

Systems consistent with the present invention shield a patient from capacitive currents that arise as a result of patient immersion into a time-varying magnetic field. The foregoing description of implementations of the invention has been presented for purposes of illustration and description. It is not exhaustive and does not limit the invention to the precise form disclosed. Modifications and variations are possible in light of the above teachings or may be acquired from practicing the invention.

The invention may be embodied in other specific forms without departing from the spirit or essential characteristics thereof. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A patient-shielding and coil system for use with a surgical navigation system that determines the position and orientation of a surgical probe within a surgical region of a patient, said patient-shielding and coil system comprising:

a coil wire electrically coupled to a source of electrical current, said coil wire operable to generate a magnetic field for use in navigating the surgical probe;

an electrically conductive surface;

insulation material situated between the coil wire and the conductive surface; and a drain wire connected to the conductive surface and forming a capacitive current loop with respect to the source, wherein capacitive current generated by said magnetic field is reduced in the patient while the magnetic field used for navigation substantially remains the same.

2. The system according to claim 1, wherein the conductive surface has a resistance of on the order of 1 ohm per square.

3. The system according to claim 1, wherein the electrically conductive surface forms a complete enclosure of the coil wire, except for a small section, so as to create an incomplete electrical circuit.

4. The system according to claim 1, wherein the conductive surface includes an upper portion and a lower portion.

5. The system according to claim 1, wherein the conductive surface includes a polyester foil, vapor deposited with aluminum.

6. The system according to claim 1, wherein the conductive surface is of a thin film material.

7. The system according to claim 1, wherein the surgical region includes a platform embedded with said coil wire for generating said magnetic field.

8. The system according to claim 1, wherein at least a portion of the coil wire is a twisted pair.

9. The system according to claim 1, wherein the magnetic field is a time varying magnetic field.

10. The system according to claim 9, wherein small residual effects of the electrically conductive surface can be eliminated by a calibration of the navigation fields.

11. The system according to claim 1, wherein a coil form surrounds a portion of the coil wire where the coil form has a rectangular shape.

12. The system according to claim 11, wherein a cross-section of said coil form is U-shaped.

13. The system according to claim 12, wherein said electrically conductive surface includes a corresponding U-shaped portion and a separate upper portion, wherein the U-shaped portion and upper portion are connected by a conductive material.

14. The system according to claim 13, wherein said upper and U-shaped electrically conductive surface defines a gap along said coil form.

15. The system according to claim 12, wherein said U-shaped coil form retains a plurality of loops of said coil wire.

16. The system according to claim 1, wherein the patient-shielding coil system is formed within an operating room table.

17. The system according to claim 1, wherein ends of said coil wire are wrapped upon one another as a twisted pair and said electrically conductive surface substantially surrounds said twisted pair.

* * * * *